United States Patent
Kishimoto et al.

(10) Patent No.: US 12,080,427 B2
(45) Date of Patent: Sep. 3, 2024

(54) DEVICE AND METHOD FOR INFERRING DEPRESSIVE STATE AND PROGRAM FOR SAME

(71) Applicant: KEIO University, Minato-ku (JP)

(72) Inventors: Taishiro Kishimoto, Shinjuku-ku (JP); Yuki Tazawa, Shinjuku-ku (JP); Liang Kuo-Ching, Shinjuku-ku (JP); Takanori Fujita, Shinjuku-ku (JP); Michitaka Yoshimura, Shinjuku-ku (JP); Momoko Kitazawa, Shinjuku-ku (JP); Masaru Mimura, Shinjuku-ku (JP)

(73) Assignee: KEIO UNIVERSITY, Tokyo (JP)

( * ) Notice: Subject to any disclaimer, the term of this patent is extended or adjusted under 35 U.S.C. 154(b) by 404 days.

(21) Appl. No.: 17/413,476

(22) PCT Filed: Dec. 13, 2019

(86) PCT No.: PCT/JP2019/048904
§ 371 (c)(1),
(2) Date: Jun. 11, 2021

(87) PCT Pub. No.: WO2020/122227
PCT Pub. Date: Jun. 18, 2020

(65) Prior Publication Data
US 2022/0059226 A1 Feb. 24, 2022

(30) Foreign Application Priority Data
Dec. 14, 2018 (JP) ................. 2018-234966

(51) Int. Cl.
*G16H 50/20* (2018.01)
*G06F 1/16* (2006.01)
*G16H 40/63* (2018.01)

(52) U.S. Cl.
CPC ............. *G16H 50/20* (2018.01); *G06F 1/163* (2013.01); *G16H 40/63* (2018.01)

(58) Field of Classification Search
CPC ........ G16H 50/20; A61B 5/103; A61B 5/165; C12Q 1/6883
(Continued)

(56) References Cited

U.S. PATENT DOCUMENTS

2013/0225575 A1* 8/2013 Lichter ................ A61K 31/506
514/264.11
2017/0238858 A1 8/2017 Yang et al.

FOREIGN PATENT DOCUMENTS

CA 2890184 A1 * 5/2014 ........... C12Q 1/6883
CN 102413871 B * 1/2016 ......... A61N 1/36082
(Continued)

*Primary Examiner* — Dilek B Cobanoglu
(74) *Attorney, Agent, or Firm* — Cozen O'Connor

(57) ABSTRACT

A method for predicting a depressive state using a wearable device. Each data type of biological data for several days from plurality of subjects is converted into data in predetermined time unit (S201). Next, quantiles of the distribution of obtained sample data are determined for each subject and each data type (S202). The standard deviation of distribution of the obtained sample data is calculated for each subject and each data type (S203). The Pearson correlation coefficient is calculated for each combination of data types for each subject (S204). Next, a prediction model for the classification problem of whether subject is in a depressive state is trained by machine leaning (S206), wherein quantiles, standard deviations, and Pearson correlation coefficients extracted from the biological data are features used for an input vector, and an evaluation of existence or non-existence of a depressive state by an expert is a label used as teacher data.

20 Claims, 6 Drawing Sheets

(58) Field of Classification Search
USPC .......................................................... 705/2
See application file for complete search history.

(56) References Cited

FOREIGN PATENT DOCUMENTS

| | | | | | |
|---|---|---|---|---|---|
| CN | 105844087 | A | * | 8/2016 | ......... A61N 1/36082 |
| CN | 106175800 | | | 12/2016 | |
| CN | 108888281 | | | 11/2018 | |
| JP | 2016-163698 | | | 9/2016 | |
| JP | 2018-15327 | | | 2/2018 | |
| JP | 2018-33795 | | | 3/2018 | |
| JP | 2018-524137 | | | 8/2018 | |
| JP | 7140348 | B2 | * | 9/2022 | ............. A61B 5/055 |
| KR | 10-1911516 | | | 10/2018 | |
| KR | 20190067774 | A | * | 6/2019 | ............. G16H 50/20 |
| WO | WO-2011109716 | A2 | * | 9/2011 | ............. A61B 5/165 |
| WO | WO-2012093143 | A1 | * | 7/2012 | ............. A61B 5/103 |

\* cited by examiner

DEVICE AND METHOD FOR INFERRING DEPRESSIVE STATE AND PROGRAM FOR SAME

RELATED APPLICATIONS

This is a U.S. National Phase Application under 35 USC 371 of International Application PCT/JP2019/048904 filed on Dec. 13, 2019.

This application claims the priority of Japanese application no. 2018-234966 filed Dec. 14, 2018, the entire content of which is hereby incorporated by reference.

FIELD OF THE INVENTION

The present invention relates to an apparatus, method and program for predicting a depressive state, and more particularly, to an apparatus, method and program for predicting a depressive state of depression or manic-depression based on biological data.

BACKGROUND OF THE INVENTION

In recent years, the patients of mental disorders have been increasing in developed countries, and the number of patients with depression or manic-depression, types of mood disorders, is particularly high. Mood disorders can be broadly divided into two categories: a depressive disorder, which includes only a depressive episode, and a bipolar disorder, which includes a symptom known as a manic episode.

It is said that a depressive state due to depression or manic-depression generally causes a decrease in energy and the patient becomes inactive. Patent Document 1 discloses a technology for determining that a subject has a bipolar disorder when a predetermined conditional formula is satisfied based on an activity level and a pulsation interval of the subject.

PRIOR ART

Patent Documents

Patent Document 1: JP Patent Publication No. 2018-33795

SUMMARY OF INVENTION

Technical Problem

The inventors have found that it is possible to improve the technology for determining a depressive state by utilizing a wearable device, which is expected to become popular in the future. The objective of the present invention is to provide a novel apparatus, method, and program for predicting a depressive state using a wearable device.

SUMMARY OF THE INVENTION

To achieve this objective, a first aspect of the present invention is a method for predicting a depressive state of a subject based on biological data, comprising: for each data type, converting biological data including a plurality of data types into unit time data in predetermined time unit; extracting one or more features from the unit time data; and predicting a depressive state using a predetermined prediction model, at least part of the one or more features being an input to the prediction model.

The second aspect of the present invention is the method according to the first aspect, wherein the biological data is data measured by a wearable device worn by the subject or data corresponding to the measured data.

The third aspect of the present invention is the method according to the first or the second aspect, wherein the biological data is data measured over a period of 48 hours or more or data corresponding to the measured data.

The fourth aspect of the invention is the method according to any one of the first to the third aspects, wherein the predetermined unit time is a unit of 1 hour.

The fifth aspect of the invention is the method according to any one of the first to the fourth aspects, wherein the plurality of data types includes skin temperature.

The sixth aspect of the present invention is the method according to the fifth aspect, wherein the plurality of data types further includes at least one of the following: number of steps, energy consumption, body movement, heart rate, sleep state, and UV level.

The seventh aspect of the present invention is the method according to any one of the first to the sixth aspects, wherein the one or more features include at least one of quantiles of the unit time data of each data type, a standard deviation of the unit time data of each data type, and a correlation coefficient of each combination of a plurality of data types.

The eighth aspect of the invention is the method according to any one of the first to the seventh aspects, wherein the at least part of the one or more features are selected by regularization.

The ninth aspect of the present invention is the method according to any one of the first to the eighth aspects, wherein the prediction model is a model, generated by machine learning, for predicting existence or non-existence of a depressive state.

The tenth aspect of the present invention is the method according to any one of the first to the eighth aspects, wherein the prediction model is a model, generated by machine learning, for predicting a rated severity of depressive state.

The eleventh aspect of the invention is the method according to the tenth aspect, wherein the rated severity is a HAMD score.

The twelfth aspect of the invention is the method according to the tenth or the eleventh aspect, wherein the biological data is data measured over a period of 72 hours or more or data corresponding to the measured data.

A thirteenth aspect of the present invention is a program for causing a computer to perform a method for predicting a depression state of a subject based on biological data, the method comprising: for each data type, converting biological data including a plurality of data types into unit time data in predetermined time unit; extracting one or more features from the unit time data; and predicting a depressive state using a predetermined prediction model, at least part of the one or more features being an input to the prediction model.

The fourteenth aspect of the present invention is an apparatus for predicting a depressed state of a subject based on biological data, configured to: for each data type, convert biological data including a plurality of data types into unit time data in predetermined time unit; extract one or more features from the unit time data; and predict a depressive state using a predetermined prediction model, at least part of the one or more features being an input to the prediction model.

A fifteenth aspect of the present invention is a method for generating a prediction model for predicting a depressive state based on biological data of a plurality of subjects, comprising: for each subject, converting each data type of biological data including a plurality of data types into unit time data in a predetermined time unit; for each subject, extracting one or more features from the unit time data; extracting one or more features from the unit time data; and generating the prediction model by machine learning, at least part of the one or more features of each subject being used for an input vector and a diagnosis result by an expert with respect to each subject being a label used as teacher data.

The sixteenth aspect of the invention is the method according to the fifteenth aspect, wherein the machine learning is ensemble learning.

The seventeenth aspect of the present invention is the method of the fifteenth or sixteenth aspect, wherein the one or more features include at least one of quantiles of the unit time data of each data type, standard deviation of the unit time data of each data type, and correlation coefficient of each combination of the plurality of data types.

The eighteenth aspect of the invention is the method of any one of the fifteenth to seventeenth aspects, wherein the at least part of the one or more features is selected by regularization.

The nineteenth aspect of the present invention is a program for causing a computer to perform a method of generating a prediction model for predicting a depressive state based on biological data of a plurality of subjects, the method comprising: for each subject, converting each data type of biological data including a plurality of data types into unit time data in a predetermined time; extracting one or more features from the unit time data for each subject; and generating the prediction model by machine learning, at least part of the one or more features of each subject being used for an input vector and a diagnosis result by an expert with respect to each subject being a label used as teacher data.

The twentieth aspect of the present invention is an apparatus for generating a prediction model for predicting a depressive state based on biological data of a plurality of subjects, configured to: for each subject, convert each data type of the biological data including a plurality of data types into unit time data in a predetermined unit of time; for each subject, extract one or more features from the unit time data; and generate the prediction model by machine learning, at least part of the one or more features of each subject being used for an input vector and a diagnosis result by an expert with respect to each subject being a label used as teacher data.

According to one aspect of the present invention, biological data including a plurality of data types is obtained using a wearable device to predict a depressive state using one or more features based on the biological data, thereby improving conventional prediction technologies.

DETAILED DESCRIPTION OF THE DRAWINGS

The following is a detailed description of the embodiment of the invention with reference to the drawings.

First Embodiment

In the first embodiment of the present invention, a product called Silmee (registered trademark) W20, which is a wristband type, comprising an accelerometer, a pulse sensor, a UV sensor, and a temperature sensor, was used as a wearable device. The accelerometer provides biological data with respect to the number of steps, energy consumption, body movement, and sleep state. The UV sensor provides UV levels. The temperature sensor provides biological data with respect to skin temperature.

The biological data with respect to the sleep state obtained from the accelerometer can be obtained by determining that a person is awake if the value calculated from the accelerations in the directions of respective axes of a triaxial accelerometer exceeds a predetermined threshold, and determining that the person is asleep if the value does not exceed the threshold, in the same way as the method known as actigraphy. As an example, the sleep state at each time or point in time, at which a value of the acceleration sensor is recorded, is expressed by 1 in a sleeping state and expressed by 0 in an awake state. A period for which the value continues to be 1 can be evaluated as sleep time, and the start time and the end time can be respectively evaluated as bedtime and wake-up time. In addition, as an example, the evaluation of the sleep state may reflect values such as heart rate other than those from the acceleration sensor.

The biological data with respect to skin temperature obtained from the temperature sensor can be obtained more specifically by measuring the skin temperature of the wrist or other part of the body where the wearable device 110 is worn. Although accurate body temperature, called core temperature, can be obtained by measuring rectal temperature, axillary temperature, etc., the skin temperature measured in this embodiment is less burdensome for the subject to measure and makes continuous data acquisition practically possible.

Figure 1:
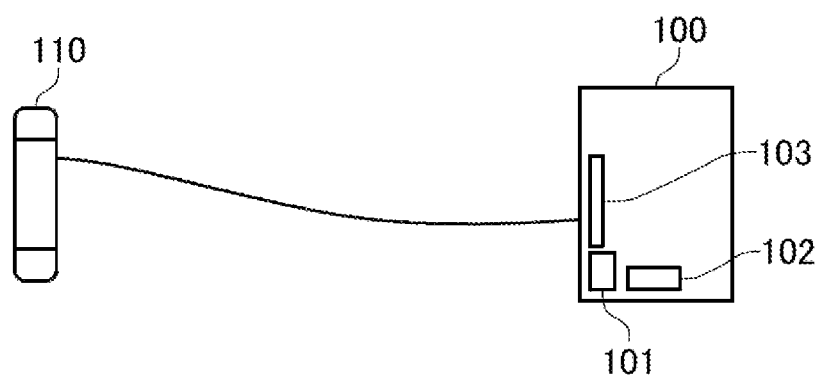
FIG. 1 shows the apparatus according to the first embodiment of the present invention.

FIG. 1 shows an apparatus according to the present embodiment. The apparatus 100 is wired or wirelessly connected to the wearable device 110 and receives biological data obtained by the wearable device 110. Other than directly receiving biological data as shown, the apparatus 100 may receive data via mobile terminal when the wearable device 110 is connected to the mobile terminal such as a smartphone, receive data via a server when the wearable device 110 is connected to the server on an IP network such as the Internet, or have the obtained biological data input to the apparatus 100 via a USB cradle.

The apparatus 100 comprises a processing unit 101 such as a processor, a CPU, etc., a storage unit 102 including a storage apparatus or a storage medium such as a memory, a hard disk, etc., and a communication unit 103 such as a communication interface for communicating with other device in a wired or wireless manner, and can be configured by executing a program for performing each process by the processing unit 101. The apparatus 100 may include one or more apparatuses, computers or servers, and the program may include one or more programs, and may be stored on a computer-readable storage medium to form a non-transitory program product.

In this embodiment, first, a prediction model for predicting the existence or non-existence of depression is generated by machine learning using biological data obtained by the wearable devices 110 from a plurality of subjects. The prediction model is then used to predict the depressive state of a new subject. In the following, the generation of the prediction model and the prediction using the prediction model will be explained separately. It is assumed that the generation of the prediction model and the prediction using the prediction model can be performed in different computers, although both are described as processes in the apparatus 100. The method according to the present embodiment is useful for screening depressive states, and can be used especially in medical examinations in occupational health.

Generating a Prediction Model

Biological data for m days (m is a positive number) from l subjects (l is a positive integer) is converted into data in a predetermined time unit, such as 1 hour, for each data type (hereinafter referred to as "unit time data") (S201). The data types included in the biological data include number of steps, energy consumption, body movement, heart rate, sleep state, skin temperature, and UV level. The data types may also be referred to as modalities. As an example, values integrated over a predetermined time period may be the unit time data for the number of steps, energy consumption, body movement, and sleep state, i.e., sleep time, and the average values over a predetermined time period may be the unit time data for heart rate, skin temperature, and UV level. The values integrated over a predetermined time period may be the unit time data for the heart rate, skin temperature, and UV level.

Next, for each subject and for each data type, n quartiles (n is a positive integer) of the distributions of the 24 m sample data obtained are determined (S202). For example, assuming n=5, five quartiles are stored: the 5th quartile, the 25th quartile, the 50th quartile, the 75th quartile, and the 95th quartile. This example assumes that the unit time data is in the unit of 1 hour.

For each subject and for each data type, the standard deviations of the distributions of the obtained 24 m sample data is calculated (S203).

Then, for each subject, the correlation coefficient, such as Pearson correlation coefficient, is calculated for each combination of data types (S204). If there are seven data types as described above, there are 21 combinations. Here, the quartiles, standard deviations, and Pearson correlation coefficients are explained in this order, but the order can be different.

Next, the prediction model for the classification problem of whether a subject is in a depressive state is trained by machine learning using the results of l-1 subjects as supervisory data, the features of the quantiles, standard deviations, and correlation coefficients extracted from the biological data of each subject being an input or an input vector, and the evaluation of the existence or non-existence of depression by an expert such as a doctor for each subject being a label (S206). The generated prediction model is stored in the storage unit 102 of the apparatus 100 that performs the prediction using the prediction model, or in a storage medium or storage device accessible from the apparatus 100.

A subset, which is part of the extracted features, can be selected for example by a type of regularization, such as L1 regularization, L2 regularization or Elastic Net, which is a combination of these (S205), and this can be used as the input vector. Machine learning can be performed by ensemble learning, such as XGBoost, which is a type of gradient boosting.

Cross validation of the generated prediction model is performed using the result of the one person excluded from the teacher data. It should be noted that the validation of the prediction model is not necessarily limited to this kind of leave-one-out cross validation (LOOCV). A specific example is k-fold cross validation, which is a method of dividing the teacher data into k portions and repeating the validation k times using one of the divided sets of data. Since the validation method affects the data used for training, it also affects the accuracy of the generated prediction model. The k-fold cross validation generally mitigates the overfitting problem compared to LOOCV.

Prediction Using a Prediction Model

Biological data for m' days (m' is a positive number) of a subject to be determined for the existence or non-existence of depression is converted into unit time data for each data type (S301). The conversion to the unit time data is performed for example by converting the biological data measured by the wearable device 110, or the data corresponding to the biological data to which processing by the wearable device 110 or the apparatus 100 is performed, into data in the unit of 1 minute and then further converted into data in the unit of 1 hour, and a variety of methods can be used. This is also true for the generation of the prediction model. However, it is desirable that the unit time for prediction is equal to the unit time for generation.

Then, for each data type, the features are extracted and stored (S302). If necessary, a subset of the features is selected, and the existence or non-existence of depression is predicted using a pre-generated prediction model with the features or their subset being an input or an input vector (S303).

In the above description, a specific product is used as an example of a wearable device, but it can be any wearable device with an accelerometer, a pulse sensor, an ultraviolet sensor, and a temperature sensor. It is preferable for the wearable device to at least comprise a temperature sensor that is considered to be contributing significantly to the high accuracy of the prediction model.

It is to be noted that if the term "only" is not written, such as in "based only on x", "in response to x only", or "in case of x only", in the present specification, it is assumed that additional information may also be taken into account. Also, as an example, it is to be noted that a description "b is performed in case of a" does not necessarily mean "b is always performed in case of a" except where expressly stated.

In addition, as a caveat, even if there are characteristics of a method, a program, a terminal, an apparatus, a server or a system (hereinafter referred to as "method, etc.") that perform operations different from those described herein, each aspect of the invention is intended to perform the same operation as one of the operations described herein, and the existence of an operation different from those described herein does not mean that the method, etc. is outside the scope of each aspect of the invention.

EXAMPLE 1-1

Biological data of 62 subjects for more than 2 days were acquired using the Silmee W20, and the prediction model was generated by the method according to the present embodiment. The predicted model was validated by leave-one-out cross-validation. The prediction results of the existence or non-existence of a depressive state using the prediction model and the diagnosis results by doctors are shown in the following table. For the biological data, two or more days out of the six days before the diagnosis date were used, and subset selection by Elastic Net and machine learning by XGBoost were performed. The unit time data were values in the unit of 1 hour.

TABLE 1

|  | healthy (prediction) | depression (prediction) |
|---|---|---|
| healthy (diagnosis) | 24 | 6 |
| depression (diagnosis) | 3 | 29 |

The Hamilton Depression Rating Scale HAMD, a general diagnostic index for depression, was used to diagnose depression by doctors. In this example, the cutoff was set at 7 in HAMD17, and the patient was judged to be in depression when the score exceeded 7. The accuracy, recall, and specificity of the test were 0.854, 0.906, and 0.800, respectively.

This example shows that the depression states are predicted with high accuracy, and that it is possible to screen healthy people and depression patients. The combination of skin temperature, which has never been pointed out to be useful for predicting a depression state as far as the inventors know, with heart rate, etc., which have been pointed out before, is thought to be contributing to the realization of high accuracy. Therefore, it is preferable to include two or more data types as biological data, including skin temperature and at least one of the following: number of steps, energy, body movement, heart rate, sleep state, and UV level.

EXAMPLE 1-2

Under the same conditions as in Example 1-1, biological data for 55 subjects were obtained for at least three of the six days prior to the diagnosis date, and the following table shows the results of the prediction model generation and the depression state prediction using the method according to the present embodiment.

TABLE 2

|  | healthy (prediction) | depression (prediction) |
|---|---|---|
| healthy (diagnosis) | 22 | 4 |
| depression (diagnosis) | 4 | 25 |

The accuracy, recall, and specificity were 0.855, 0.862, and 0.846, respectively.

Although this example shows that the depressive states are predicted with high accuracy, there is no significant improvement in accuracy compared to the prediction of the existence or non-existence of depression using two days of biological data. It can be said that, in the method according to the present embodiment, sufficiently high accuracy can be obtained when 2 days or 48 hours of biological data is used. This leads to a reduction in the period of time that a subject has to wear the wearable device 110, and the shorter time of wearing and smaller burden on the subject encourage widespread use of the screening for early detection of depression.

EXAMPLE 1-3

Biological data of 86 subjects for more than 3 days were acquired using the Silmee W20, and the prediction model was generated by the method according to the present embodiment. The prediction model was validated by 10-fold cross-validation. The following table shows the results of the comparison the prediction results of the presence of a depressive state using the prediction model with the diagnosis results by doctors. The biological data were obtained by dividing 228 sample data from 86 subjects into 10 portions. Here, data from the same subject were made to be within the same set (fold). In addition, multiple data sets were obtained from some subjects. No selection of a subset was made, and machine learning by XGBoost was done. The unit time data were values in the unit of 1 hour.

TABLE 3

|  | healthy (prediction) | depression (prediction) |
|---|---|---|
| healthy (diagnosis) | 96 | 23 |
| depression (diagnosis) | 37 | 72 |

The accuracy, recall, and specificity were 0.737, 0.661, and 0.807, respectively. Although the relaxation of overfitting due to the change of the verification method from LOOCV to 10-fold cross-validation may have caused a slight decrease in the accuracy, etc., the prediction was still performed with high accuracy.

In the generated prediction model, the following table shows the calculation results of the importance (importance) of each feature, which indicates which features contribute significantly to the prediction result. Specifically, the importance of each feature is estimated by calculating how much the model accuracy improves when a certain feature is changed. We used Azure Machine Learning (trademark), a service provided by Microsoft. The values of importance of all features add up to 1.

TABLE 4

|  | feature | importance |
|---|---|---|
| 1 | correlation coefficient between sleep state and skin temperature | 0.0453 |
| 2 | skin temperature-50% | 0.0439 |
| 3 | body movement-standard deviation | 0.0434 |
| 4 | number of steps-95% | 0.0388 |
| 5 | correlation coefficient between sleep state and UV level | 0.0364 |
| 6 | body movement-50% | 0.0312 |
| 7 | sleep state-50% | 0.0296 |
| 8 | skin temperature-5% | 0.0292 |
| 9 | correlation coefficient between energy consumption and heart rate | 0.0278 |
| 10 | correlation coefficient between skin temperature and heart rate | 0.0271 |

The correlation coefficient between sleep state and skin temperature, the 50th quantile of skin temperature, and the standard deviation of body movement were found to be highly important features, confirming that the contribution of skin temperature is significant. In addition, the contribution of the correlation coefficient between skin temperature and sleep state was also significant, indicating that it is desirable to include sleep state in addition to skin temperature as biological data.

Second Embodiment

The second embodiment of the present invention enables prediction of the severity of a depressive state, in addition to the existence or non-existence of a depressive state, or alternatively to the existence or non-existence of a depressive state. First, a prediction model for predicting the severity of a depressive state is generated by machine learning using biological data obtained from a plurality of subjects by wearable devices 110. Then, the prediction model is used to predict the severity of a depressive state in a new subject.

Figure 2:
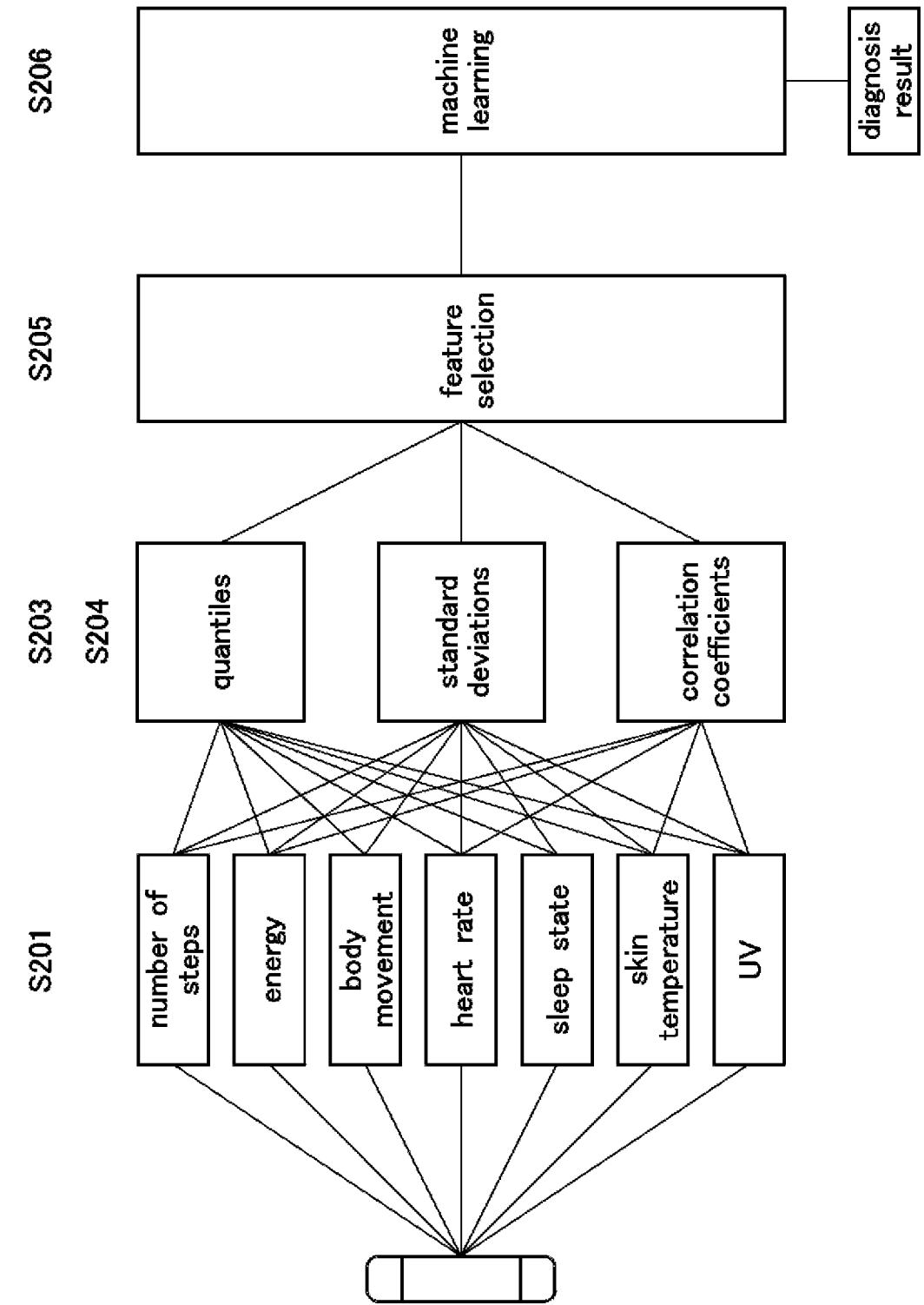
FIG. 2 illustrates the generation process of a prediction model according to the first embodiment of the present invention.

The generation of the prediction model in this embodiment is similar to that described in the first embodiment with reference to FIG. 2, with the differences that the doctor's diagnosis result used in the machine learning is not the existence or non-existence of a depressive state but the score of the severity of a depressive state, and the algorithm used in the machine learning is not an algorithm suitable for classification problems but an algorithm suitable for regression problems.

Figure 3:
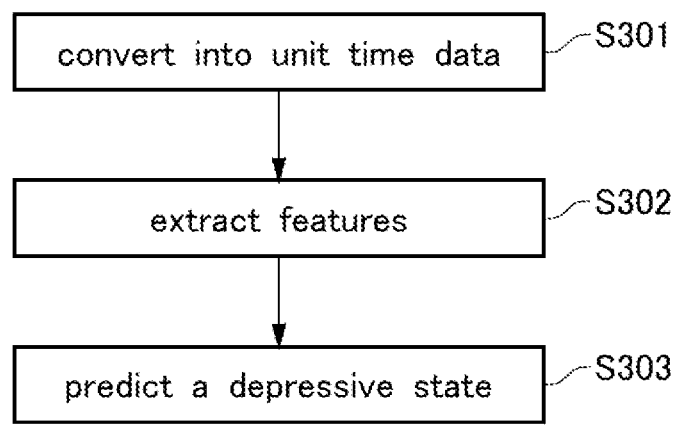
FIG. 3 illustrates the prediction process using the prediction model according to the first embodiment of the present invention.

The prediction using the prediction model in this embodiment is similar to that described with reference to FIG. 3 in the first embodiment, with the difference that the output is not the existence or non-existence of a depressive state but the severity of a depressive state.

For the severity of a depressive state, the Hamilton Depression Rating Scale HAMD can be used. There are several versions of the scale. In HAMD 17, a doctor or other specialist evaluates 17 items, and for each item there is a score from 3 to 5. For example, a diagnosis is made by judging that a score of up to 7 is normal, 8 to 13 is mild, 14 to 18 is moderate, 19 to 22 is severe, and 23 or more is the most severe.

Using the method according to the present embodiment, the severity of a depressive state can be determined so that it can contribute to making precise decisions necessary for a treatment, such as decisions on treatment policies for a depressive state and changes in prescribed medications. This is highly beneficial in assisting diagnoses and treatments in psychiatric clinical practice.

EXAMPLE 2-1

Figure 4:
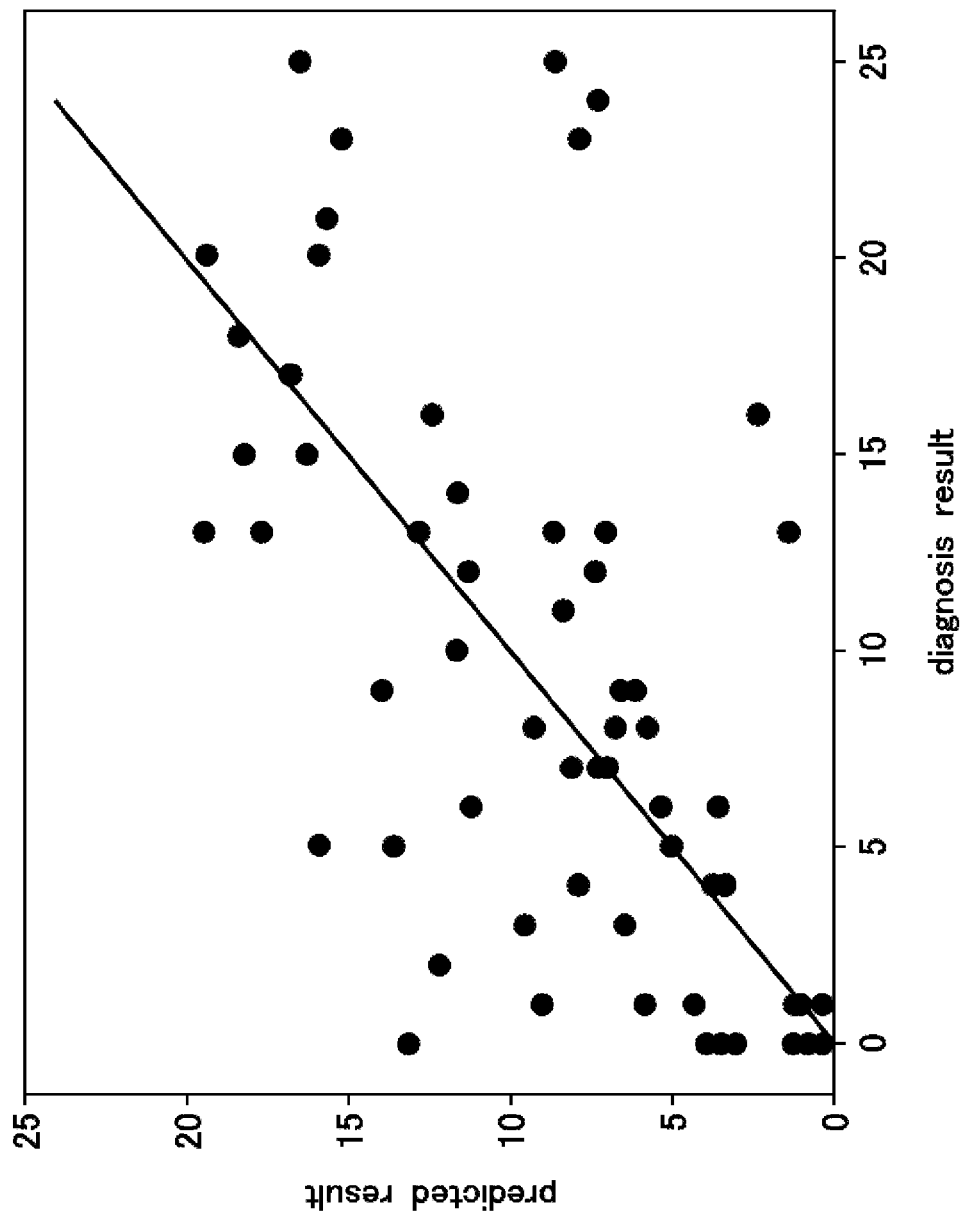
FIG. 4 shows the accuracy of the prediction result of Example 2-1.

Biological data of 62 subjects for more than 2 days were acquired using the Silmee W20, and the prediction model was generated by the method according to the present embodiment. The prediction model was validated by leave-one-out cross-validation. The prediction results of the existence or non-existence of a depressive state using the prediction model and the diagnosis results by doctors are shown in FIG. 4. For the biological data, two or more days out of the six days prior to the diagnosis date were used, and subset selection by Elastic Net and machine learning by XGBoost were performed. The unit time data were values in the unit of 1 hour The mean absolute error was 4.11, the correlation coefficient was 0.604, the p-value was $2.04 \times 10^{-7}$, and the $R^2$ was 0.341.

EXAMPLE 2-2

Figure 5:
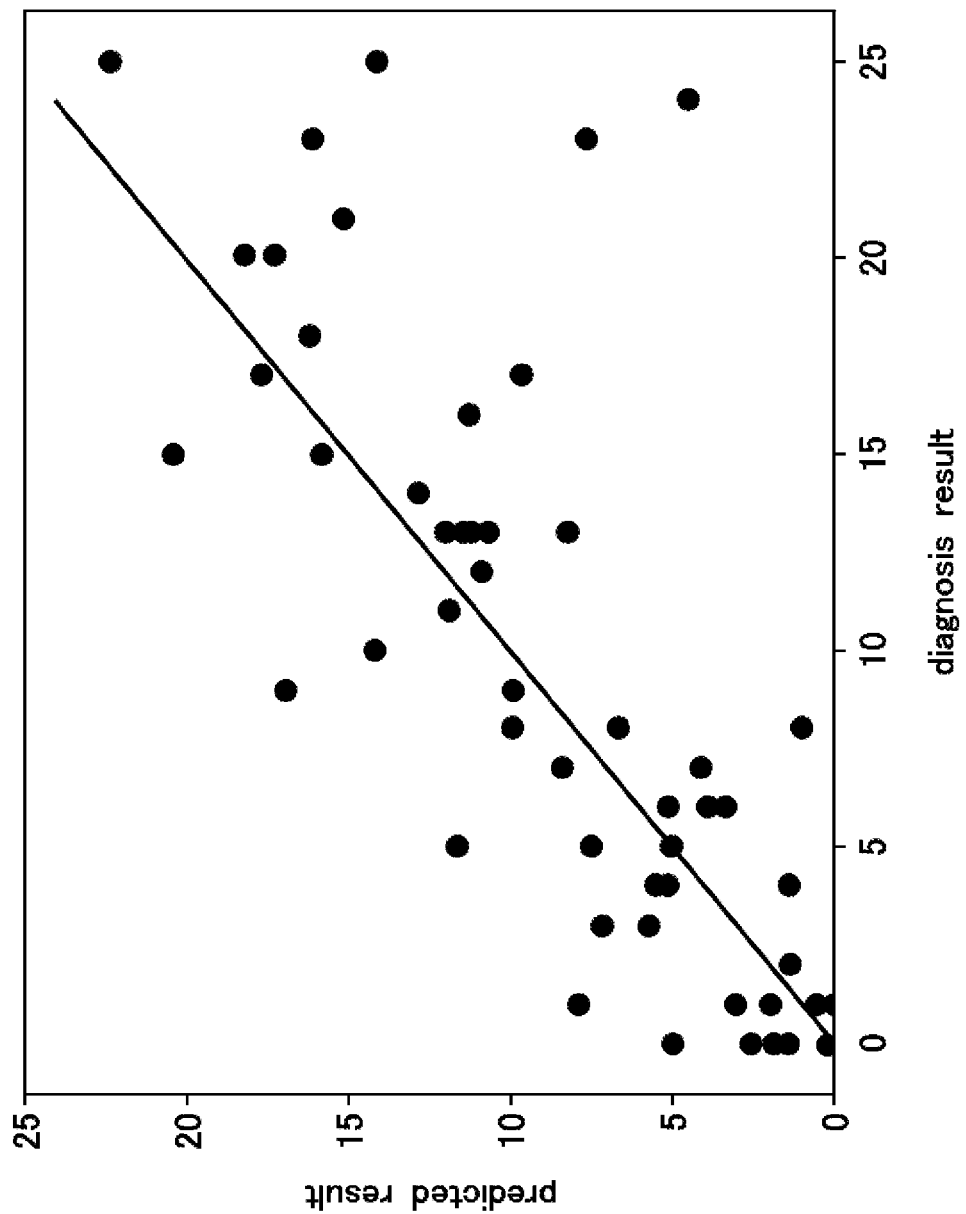
FIG. 5 shows the accuracy of the prediction result of Example 2-2.

Under the same conditions as in Example 2-1, biological data for more than three days were obtained for 55 subjects, and the results of the generation of the prediction model and the prediction of the severity of a depressive state using this method are shown in FIG. 5.

The mean absolute error was 3.29, the correlation coefficient was 0.763, and the p-value was $1.22 \times 10^{-11}$. $R^2$ was 0.570. This result shows a higher correlation coefficient than that of Example 2-1, indicating that in predicting the severity, it is highly likely that about 3 days, or 72 hours, or more of wearing time is necessary to obtain a high prediction accuracy of over 0.700. This means that, in contrast to Examples 1-1 and 1-2, it is preferable to generate the model for predicting the severity of a depressive state using biological data measured for a longer period of time than the model for predicting the existence or non-existence of a depressive state.

EXAMPLE 2-3

Figure 6:
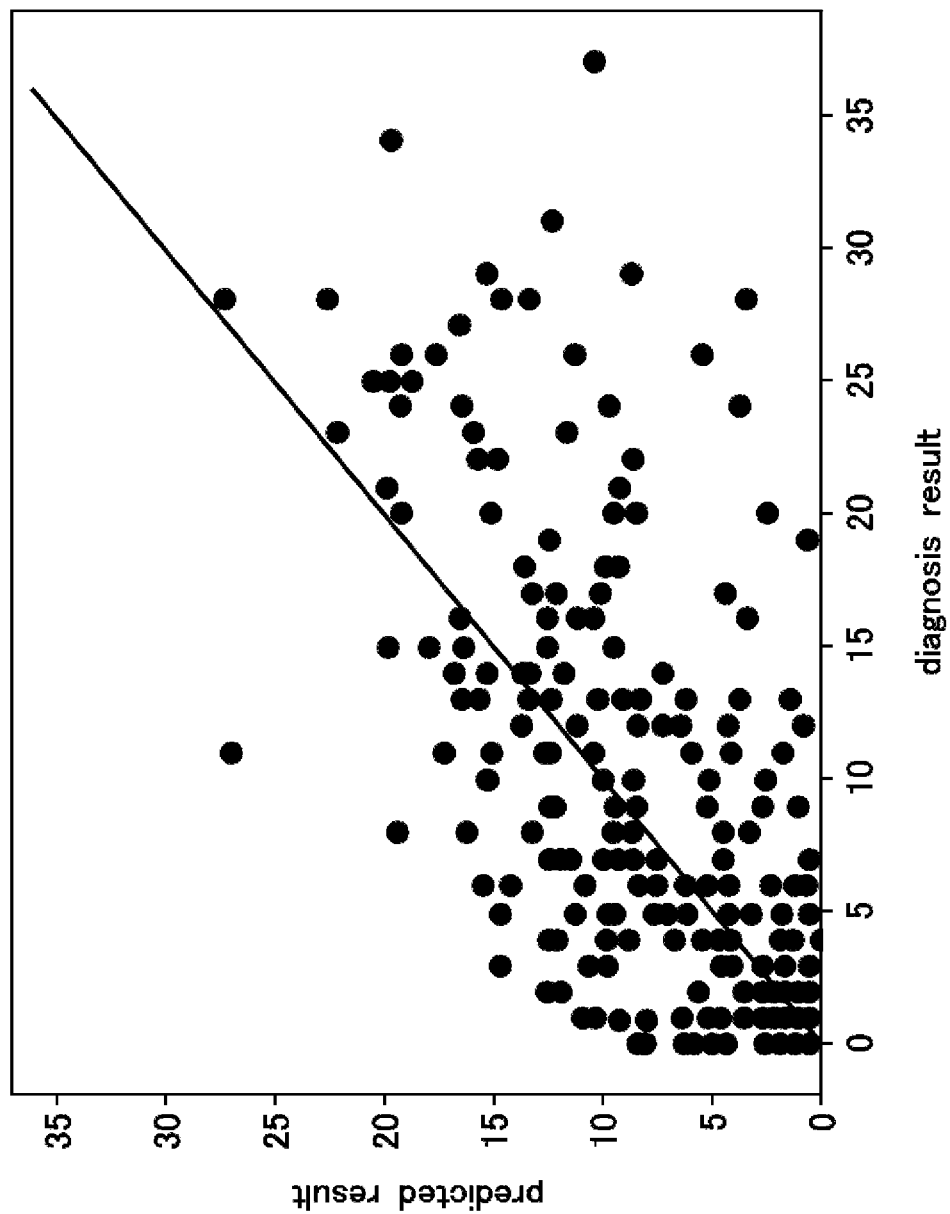
FIG. 6 shows the accuracy of the prediction result of Example 2-3.

Biological data of 86 subjects for more than 7 days were acquired using the Silmee W20, and the prediction model was generated by the method according to the present embodiment. The prediction model was validated by 10-fold cross-validation. The prediction results of the existence or non-existence of a depressive state using the prediction model and the diagnosis results by doctors are shown in FIG. 6. The biological data were obtained by dividing 236 sample data from 86 subjects into 10 portions. Here, data from the same subject were made to be within the same set (fold). In addition, multiple data sets were obtained from some subjects. No subset selection was done, and machine learning by XGBoost was done. The unit time data were values in the unit of 1 hour.

The mean absolute error was 4.94, the correlation coefficient was 0.610, and the p-value was $2.20 \times 10^{-16}$, with an $R^2$ of 0.372. The R2 is 0.372. The relaxation of overshooting by changing the verification method from LOOCV to 10-fold cross-validation may have caused a slight decrease in the correlation coefficient and other parameters, but the prediction is still highly accurate.

The following table shows the calculation result of the importance of each feature in the generated prediction model, which indicates which features contribute significantly to the prediction result, using the Azure Machine Learning (trademark) service provided by Microsoft. The values of importance of all features add up to 1.

TABLE 5

| | feature | importance |
|---|---|---|
| 1 | skin temperature-95% | 0.0340 |
| 2 | correlation coefficient between sleep state and skin temperature | 0.0288 |
| 3 | skin temperature-50% | 0.0284 |
| 4 | correlation coefficient between sleep state and heart rate | 0.0283 |
| 5 | correlation coefficient between energy consumption and body movement | 0.0275 |
| 6 | correlation coefficient between heart rate and UV level | 0.0268 |
| 7 | energy consumption-95% | 0.0259 |
| 8 | body movement-50% | 0.0250 |
| 9 | skin temperature-5% | 0.0249 |
| 10 | energy consumption-50% | 0.0249 |

The 95th quartile of skin temperature, the correlation coefficient between sleep state and skin temperature, and the 50th quartile of skin temperature were found to be highly important features, and as in Example 1-3, the contribution of skin temperature was confirmed to be significant. Also, as in Example 1-3, the contribution of the correlation coefficient between skin temperature and sleep state is also significant, and it can be said that it is preferable to include sleep state in addition to skin temperature as biological data.

REFERENCE SIGNS LIST 100 apparatus
101 processing unit
102 storage unit
103 communication unit
110 wearable device

The invention claimed is:

1. A method for operating an automated diagnostic system to predict a depressive state of a subject, the automated diagnostic system including a computer with a non-transitory computer-readable storage medium and processor, the method comprising:
receiving, by the automated diagnostic system, biological data of the subject measured by a wearable device worn by the subject, the biological data comprising a plurality of data types;
converting, by the automated diagnostic system, the biological data of each data type into unit time data in a predetermined time unit, the unit time data for each data type including a statistical representation of the biological data over a predefined period of time;
extracting, by the automated diagnostic system, a set of features from the unit time data to produce a feature vector, the set of features including a statistical distribution information of the unit time data for each data type and a correlation coefficient for each pairwise combination of the plurality of data types; and
providing, by the automated diagnostic system, the feature vector as an input to a trained prediction model and producing, by the trained prediction model, an output indicating whether the subject exhibits a depressive state, the trained prediction model being trained using a set of labeled training data which includes feature vectors corresponding to biological data of a plurality of training subjects with predetermined diagnosis states as labels indicative of the depressive state.

2. The method according to claim 1, wherein the predetermined time unit is a unit of 1 hour.

3. The method according to claim 1, wherein the plurality of data types includes skin temperature.

4. The method according to claim 3, wherein the set of features includes quantiles of skin temperature.

5. The method according to claim 3, wherein the plurality of data types further includes sleep state.

6. The method according to claim 5, wherein the plurality of data types further includes a number of steps, energy consumption, body movement, heart rate and UV level.

7. The method according to claim 1, wherein the plurality of data types includes skin temperature and sleep state, and wherein the set of features includes a correlation coefficient between skin temperature and sleep state.

8. The method according to claim 7, wherein the set of features further includes quantiles of skin temperature.

9. The method according to claim 1, wherein the set of features further includes a standard deviation of the unit time data for each data type.

10. The method according to claim 1, wherein at least part of the set of features is selected by regularization.

11. The method according to claim 1, wherein the prediction model is a model, generated by machine learning, for predicting existence or non-existence of the depressive state.

12. The method according to claim 1, wherein the prediction model is a model, generated by machine learning, for predicting a rated severity of the depressive state.

13. The method according to claim 12, wherein the rated severity is a HAMD score.

14. The method according to claim 1, wherein the prediction model includes a first model, generated by machine learning, for predicting existence or non-existence of the depressive state, and a second model, generated by machine learning, for predicting a degree of severity of the depressive state, and
wherein biological data used in generation of the second model is measured in longer period than biological data used in generation of the first model.

15. A non-transitory computer-readable medium encoded with a program which, when executed by a processor of an automated diagnostic system, causes the automated diagnostic system to predict a depressive state of a subject, the program comprising:
program code for receiving, by the automated diagnostic system, biological data of the subject measured by a wearable device worn by the subject, the biological data comprising a plurality of data types;
program code for, converting, by the automated diagnostic system, the biological data of each data type into unit time data in a predetermined time unit, the unit time data for each data type including a statistical representation of the biological data over a predefined period of time;
program code for extracting, by the automated diagnostic system, a set of features from the unit time data to produce a feature vector, the set of features including a statistical distribution information of the unit time data for each data type and a correlation coefficient for each pairwise combination of the plurality of data types; and
program code for providing, by the automated diagnostic system, the feature vector as an input to a trained prediction model and producing, by the trained prediction model, an output indicating whether the subject exhibits a depressive state, the trained prediction model being trained using a set of labeled training data which includes feature vectors corresponding to biological data of a plurality of training subjects with predetermined diagnosis states as labels indicative of the depressive state.

16. The non-transitory computer-readable medium according to claim 15, wherein the plurality of data types includes skin temperature, sleep state, number of steps, energy consumption, body movement, heart rate and UV level.

17. The non-transitory computer-readable medium according to claim 15, wherein the plurality of data types includes skin temperature and sleep state; and
wherein the set of features includes a correlation coefficient between skin temperature and sleep state, and quantiles of skin temperature.

18. An apparatus for predicting a depressive state of a subject, the apparatus comprising a computer with a non-transitory computer-readable storage medium and processor, the apparatus being configured to:
receive biological data of the subject measured by a wearable device worn by the subject, the biological data comprising a plurality of data types;
convert the biological data of each data type into unit time data having a predetermined time unit, the unit time data for each data type including a statistical representation of the biological data over a predefined period of time;

extract a set of features from the unit time data to produce a feature vector, the set of features including a statistical distribution information of the unit time data for each data type and a correlation coefficient for each pairwise combination of the plurality of data types; and provide the feature vector as an input to a trained prediction model and produce, by the trained prediction model, an output indicating whether the subject exhibits a depressive state, the trained prediction model being trained using a set of labeled training data which includes feature vectors corresponding to biological data of a plurality of training subjects with predetermined diagnosis states as labels indicative of the depressive state.

19. The apparatus according to claim 18, wherein the plurality of data types includes skin temperature, sleep state, number of steps, energy consumption, body movement, heart rate and UV level.

20. The apparatus according to claim 18, wherein the plurality of data types includes skin temperature and sleep state; and wherein the one or more features include a correlation coefficient between skin temperature and sleep state, and quantiles of skin temperature.

* * * * *